US008962279B2

(12) United States Patent
Liu et al.

(10) Patent No.: US 8,962,279 B2
(45) Date of Patent: Feb. 24, 2015

(54) SOLID-PHASE CHELATORS AND ELECTRONIC BIOSENSORS

(75) Inventors: David J. Liu, Fremont, CA (US); Xing Su, Cupertino, CA (US); Kai Wu, Mountain View, CA (US)

(73) Assignee: Intel Corporation, Santa Clara, CA (US)

( * ) Notice: Subject to any disclaimer, the term of this patent is extended or adjusted under 35 U.S.C. 154(b) by 1264 days.

(21) Appl. No.: 12/655,459

(22) Filed: Dec. 30, 2009

(65) Prior Publication Data
US 2011/0159481 A1 Jun. 30, 2011

(51) Int. Cl.
C12P 19/34 (2006.01)
C12M 1/00 (2006.01)
C12Q 1/48 (2006.01)
C12Q 1/68 (2006.01)
G01N 27/414 (2006.01)

(52) U.S. Cl.
CPC .............. *C12Q 1/48* (2013.01); *C12Q 1/6837* (2013.01); *C12Q 1/6869* (2013.01); *G01N 27/4145* (2013.01); *G01N 2333/9125* (2013.01)
USPC ...................... 435/91.2; 435/283.1

(58) Field of Classification Search
CPC .............. C12Q 1/6837; C12Q 1/6869; C12Q 2525/301; C12Q 2565/507; C12Q 2565/607
USPC ............................ 435/91.2, 283.1
See application file for complete search history.

(56) References Cited

U.S. PATENT DOCUMENTS

| 5,849,487 | A | 12/1998 | Hase et al. |
| 7,211,390 | B2 | 5/2007 | Rothberg et al. |
| 7,575,865 | B2 | 8/2009 | Leamon et al. |
| 8,262,900 | B2 | 9/2012 | Rothberg et al. |
| 8,372,585 | B2 | 2/2013 | Su et al. |
| 8,444,835 | B2* | 5/2013 | Elibol et al. ................. 204/411 |
| 8,524,057 | B2 | 9/2013 | Rothberg et al. |
| 2004/0197793 | A1* | 10/2004 | Hassibi et al. .................... 435/6 |
| 2004/0229247 | A1* | 11/2004 | DeBoer et al. ..................... 435/6 |
| 2006/0105373 | A1* | 5/2006 | Pourmand et al. ................ 435/6 |
| 2006/0199193 | A1 | 9/2006 | Koo et al. |
| 2010/0167938 | A1 | 7/2010 | Su et al. |
| 2010/0330553 | A1* | 12/2010 | Su et al. ............... 435/6 |
| 2012/0061239 | A1* | 3/2012 | Elibol et al. .................. 204/406 |

OTHER PUBLICATIONS

Kim et al., Acc. Chem. Res., vol. 42, No. 1, pp. 23-31, published on web Sep. 18, 2008.*
Koo et al., U.S. Appl. No. 11/073,160, entitled "Sensor Arrays and Nucleic Acid Sequencing Applications," filed Mar. 4, 2005, 31 pages.
Su et al., U.S. Appl. No. 12/459,309, entitled "Chemically Induced Optical Signals and DNA Sequencing," filed Jun. 30, 2009, 45 pages.
Elibol et al., "Nanoscale thickness double-gated field effect silicon sensors for sensitive pH detection in fluid," Applied Physics Letters, vol. 92, No. 19, May 2008, pp. 193904-1 to 193904-3.
Kling, "Ultrafast DNA sequencing", Nature Biotechnology, Nature Publishing Group, vol. 21, No. 12, Dec. 2003, pp. 1425-1427.
Ronaghi et al., "DNA Sequencing: A Sequencing Method Based on Real-Time Pyrophosphate," Science Magazine, vol. 281, No. 5375, Jul. 17, 1998, pp. 363-365.
Carrara et al., "Interface Layering Phenomena in Capacitance Detection of DNA with Biochips," Sensors & Transducers Journal, vol. 76, Issue 2, Feb. 26, 2007, pp. 969-977.
Carrara et al., "Improving Probe Immobilization for Label-Free Capacitive Detection of DNA Hybridization on Microfabricated Gold Electrodes," Sensors & Transducers Journal, vol. 88, Issue 2, Feb. 26, 2008, pp. 31-39.
Lee et al., "Microfabricated PCR-electrochemical device for simultaneous DNA amplification and detection," Lab on a Chip, vol. 3, Apr. 17, 2003, pp. 100-105.
Daniels et al., "Label-Free Impedance Biosensors: Opportunities and Challenges," Electroanalysis, vol. 19, No. 12, 2007, pp. 1239-1257.
Wang et al., "Electrochemical Impedance Biosensor for Glucose Detection Utilizing a Periplasmic *E. coli* Receptor Protein," Electrochemical and Solid-State Letters, vol. 8, Issue 8, Jun. 7, 2005, pp. H61-H64.
Kim et al., "Chemosensors for Pyrophosphate," Accounts of Chemical Research, vol. 42, No. 1, Jan. 2009, pp. 23-31.
Ju, J. et al., "Four-color DNA Sequencing by Synthesis Using Cleavable Fluorescent Nucleotide Reversible Terminators," Proc. Natl. Acad. Sci., 2006, pp. 19635-19640, vol. 103, No. 52.
Yang, Z. et al., "Nucleoside Alpha-thiotriphosphates, Polymerases and the Exonuclease III Analaysis of Oligonucleotides Containing Phosphorothioate Linkages," Nucleic Acids Research, 2007, pp. 3118-3127, vol. 35, No. 9.
DeLucia, A.M. et al., "An Error-prone Family of Y DNA Polymerase (DinB homolog from *Sulfolobus solfataricus*) uses a 'Steric Gate' Residue for Discrimination Against Ribonucleotides," Nucleic Acids Research, 2003, pp. 4129-4137, vol. 31, No. 14.
Gao, G. et al., "Conferring RNA Polymerase Activity to a DNA Polymerase: A Single Residue in Reverse Transcriptase Controls Substrate Selection," 1997, pp. 407-411, Proc. Natl. Acad. Sci., vol. 94.

(Continued)

*Primary Examiner* — Cynthia B Wilder

(57) ABSTRACT

Methods for sequencing nucleic acids are presented. Sequencing is accomplished through the chemical amplification of the products of DNA synthesis and the detection of the chemically amplified products. In embodiments of the invention, a substrate is provided having a plurality of molecules of DNA to be sequenced attached and a plurality of molecules capable of chelating pyrophosphate ions attached, the DNA molecules to be sequenced are primed, and a next complementary nucleotide is incorporated and excised a plurality of times leading to the buildup of pyrophosphate ions locally around the DNA molecule to be sequenced. Pyrophosphate ions are captured by the substrate-attached chelators and electronically detected to determine the identity of the next complementary nucleic acid in the DNA molecule to be sequenced. Additionally, devices and methods are provided for detecting biomolecules through the detection of pyrophosphate ions.

9 Claims, 12 Drawing Sheets

(56) References Cited

OTHER PUBLICATIONS

Star, A. et al., "Electronic Detection of Specific Protein Binding Using Nanotube FET Devices," 2003, pp. 459-463, Nano Letters, vol. 3, No. 4.

Fritz, J. et al., "Electronic Detection of DNA by its Intrinsic Molecular Charge," 2002, pp. 14142-14146, Proc. Natl. Acad. Sci., vol. 99, No. 22.

Kruppa, M. et al., "Reversible Coordinative Bonds in Molecular Recognition," 2006, pp. 3520-3560, Chem. Rev., vol. 106.

Pinson, J. et al., "Attachment of Organic Layers to Conductive or Semiconductive Surfaces by Reduction of Diazonium Salts," 2005, pp. 429-439, Chemical Society Reviews, vol. 34.

Corgier, B.P. et al., "Diazonium-Protein Adducts for Graphite Electrode Microarrays Modification: Direct and Addressed Electrochemical Immobilization," 2005, pp. 18328-18332, J. Am. Chem. Soc., vol. 127.

Janicki, M. et al., "Ion Sensitive Field Effect Transistor Modelling for Multidomain Simulation Purposes," 2004, pp. 831-840, Microelectronics Journal, vol. 35.

Rolka, D. et al., "Integration of a Capacitive EIS Sensor into a FIA System for pH and Penicillin Determination," 2004, pp. 84-89, Sensors, vol. 4.

Fuller, C.W. et al., "The Challenges of Sequencing by Synthesis," 2009, pp. 1013-1023, Nature Biotechnology, vol. 27, No. 11.

Eid, J. et al., "Real-Time DNA Sequencing from Single Polymerase Molecules," 2009, pp. 133-138, Science, vol. 323.

Margulies, M. et al., "Genome Sequencing in Microfabricated High-density Picolitre Reactors," 2005, pp. 375-380, Nature, vol. 437.

\* cited by examiner

SOLID-PHASE CHELATORS AND ELECTRONIC BIOSENSORS

CROSS REFERENCE TO RELATED APPLICATIONS

The present application is related to U.S. patent application Ser. No. 11/226,696, entitled "Sensor Arrays and Nucleic Acid Sequencing Applications," filed Sep. 13, 2005, now pending, which is a continuation-in-part application that claims the benefit of U.S. patent application Ser. No. 11/073, 160, entitled "Sensor Arrays and Nucleic Acid Sequencing Applications," filed Mar. 4, 2005, and is also related to U.S. patent application Ser. No. 12/319,168, entitled "Nucleic Acid Sequencing and Electronic Detection," filed Dec. 31, 2008, and U.S. patent application Ser. No. 12/459,309, entitled "Chemically Induced Optical Signals," filed Jun. 30, 2009, now pending, the disclosures of which are incorporated herein by reference.

BACKGROUND OF THE INVENTION

1. Field of the Invention

The embodiments of the present invention relate generally to methods and devices for the detection of nucleic acids and other biomolecules, including the electronic detection of nucleic acid sequencing reactions, nucleic acid sequencing, and solid-phase chelators that are useful in electronic biomolecule detection.

2. Background Information

Genetic information in living organisms is contained in the form of very long nucleic acid molecules such as deoxyribonucleic acid (DNA) and ribonucleic acid (RNA). Naturally occurring DNA and RNA molecules are typically composed of repeating chemical building blocks called nucleotides which are in turn made up of a sugar (deoxyribose or ribose, respectively), phosphoric acid, and one of four bases, adenine (A), cytosine (C), guanine (G), and thymine (T) or uracil (U). The human genome, for example, contains approximately three billion nucleotides of DNA sequence and an estimated 20,000 to 25,000 genes. DNA sequence information can be used to determine multiple characteristics of an individual as well as the presence of and or susceptibility to many common diseases, such as cancer, cystic fibrosis, and sickle cell anemia. Determination of the entire three billion nucleotide sequence of the human genome has provided a foundation for identifying the genetic basis of such diseases. A determination of the sequence of the human genome required years to accomplish. Sequencing the genomes of individuals provides an opportunity to personalize medical treatments. The need for nucleic acid sequence information also exists in research, environmental protection, food safety, biodefense, and clinical applications, such as for example, pathogen detection (the detection of the presence or absence of pathogens or their genetic varients).

Thus, because DNA sequencing is an important technology for applications in bioscience, such as, for example, the analysis of genetic information content for an organism, tools that allow for faster and or more reliable sequence determination have great utility. Applications such as, for example, population-based biodiversity projects, disease detection, personalized medicine, prediction of effectiveness of drugs, and genotyping using single-nucleotide polymorphisms, stimulate the need for simple and robust methods for sequencing short lengths of nucleic acids (such as, for example, those containing 1-20 bases). Sequencing methods that provide increased accuracy and or robustness, decreased need for analysis sample, and or high throughput are valuable analytical and biomedical tools.

DETAILED DESCRIPTION OF THE INVENTION

Embodiments of the present invention provide devices and methods that are useful for biosensing applications such as, for example, disease detection, bacterial and virus detection, and sequencing and detecting nucleic acids in general. Methods are provided according to embodiments of the invention by which whole genomes of organisms can be sequenced. Additionally, according to methods of the invention, diseases are detected, for example, by assaying metabolic enzyme activities. Bacterial viability is detected, for example, by measuring released ATP. In embodiments of the invention, sensors comprise surface-attached chelators that are capable of chelating reaction products and sensors comprise devices capable of detecting the chelation of a reaction product.

Methods are provided for sequencing nucleic acids in which amplification of the nucleic acid sample (i.e., increasing the number of copies of the nucleic acid molecules in the sample) optionally does not have to occur. As much as one third of the error during the sequencing of a nucleic acid sample has been reported to be due to errors introduced during the amplification of the nucleic acid sample. By not amplifying a nucleic acid sample to be sequenced, amplification-related errors can be avoided. Additionally, avoiding amplifying a sample avoids the concentration bias that can develop when a sample is amplified. The concentration bias that occurs during amplification is a result of the selective amplification advantage found for certain sequence populations, such that some sequences are amplified preferentially to a greater extent than other sequences. Because amplification-related errors are reduced, the methods of the present invention are useful for surveying for rare mutations among samples having a variety of components (i.e., mixed background components).

Figure 1:
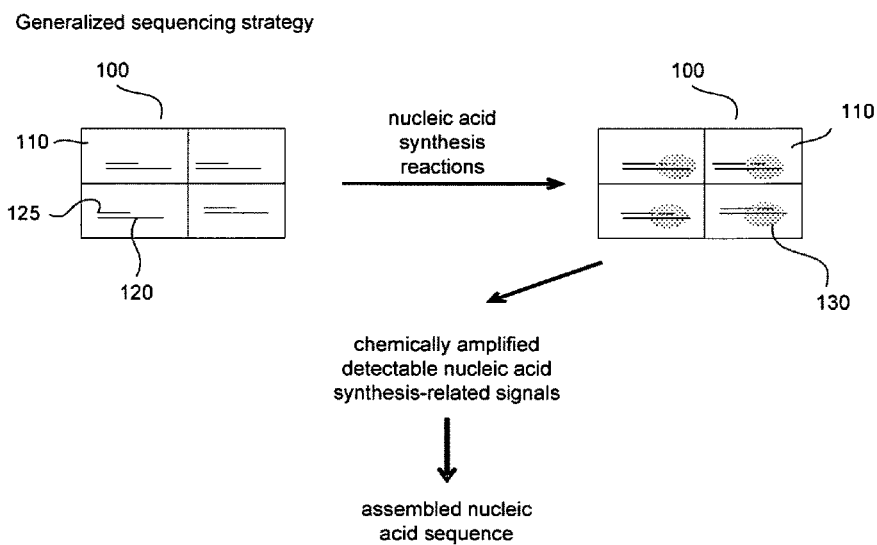
FIG. 1 provides a simplified diagram of a method for the parallel sequencing of nucleic acids employing chemical signal amplification and automatable detection of chemically amplified sequencing reactions.

FIG. 1 depicts a generalized nucleic acid sequencing strategy according to embodiments of the invention. In FIG. 1, an array of detection regions 100, such as, for example, electronic having reaction (detection) regions 110 and immobilized DNA molecules 120 is shown. One DNA molecule to be sequenced is immobilized per detection region 110 in this example. Before sequencing a sample of DNA, overlapped DNA fragments are immobilized randomly on the surface of a substrate so that statistically one DNA molecule 120 occupies the reaction region 110. A sample of DNA is optionally fragmented into smaller polymeric molecules using, for example, restriction enzymes or mechanical forces (shearing). The immobilized nucleic acid is primed with a primer 125 that is terminated with a nuclease resistant base and nucleic acid synthesis and deconstruction reactions are performed and amplified chemical products of the synthesis reactions 130 are created in the detection regions 110. The identified base position is then filled with a matching nuclease resistant base, and the reaction is repeated to determine a matching base for the next available position on the DNA strand 120. These elements of the method (identification of a base position and filling the position with a nuclease-resistant version of the matching base that has been determined by the identification reaction) are repeated to determine sequence information for the attached DNA strand 120. The number of times the reaction is repeated depends on the number of bases of DNA to be sequenced. In this example, the amplified chemical products 130 are detected electronically and sequence data for the immobilized DNA molecules are assembled. Amplified chemical products in a reaction and detection region 110, such as, for example, a gate of a FET, alter the current flow and capacitance between the source and the drain allowing electronic detection of the amplified products. Detected reaction products and their corresponding positions in the array are recorded and analyzed using a computer and analysis software. Data from regions having no immobilized nucleic acid sample or a plurality of immobilized samples are distinguished. Additionally, a computer is optionally used not only to address and monitor the reaction regions of the array, but also to provide reagents to the array from fluidicly coupled resevoirs. In some embodiments the array is a chip comprising integrated electronics and or part of a microfluidic device or a microfluidic device coupled to a chip or computer having electronics that are capable of performing some or all of the features of addressibly monitoring reaction regions (recording signals from reaction regions) and addressibly supplying reagents to reaction regions.

Figure 2:
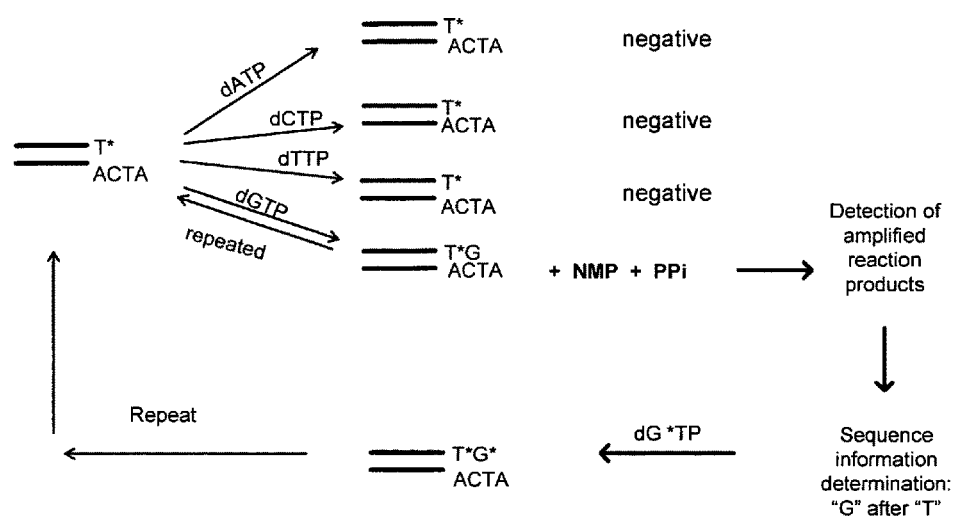
FIG. 2 outlines a general nucleic acid sequencing strategy using the chemical amplification of nucleic acid synthesis reaction products and the detection of amplified reaction products to assemble sequence information.

FIG. 2 diagrams a method for providing amplified chemical signals and sequencing data for nucleic acid sequencing reactions. In FIG. 2, a DNA molecule to be sequenced is primed with a primer that is terminated with an exonuclease resistant nucleotide. The chemical products resulting from the incorporation of a complementary dNTP (a deoxynucleotide triphosphate, e.g., dATP (deoxyadenosine triphosphate), dCTP (deoxycytidine triphosphate), dGMP (deoxyguanosine triphosphate), or dTMP (deoxythymidine triphosphate), for example) into a nucleic acid strand to be sequenced are amplified through the repeated addition and excision of the next complementary nucleotide. In one embodiment, individual test reactions are performed using one of four dNTPs and a determination is made regarding the next complementary nucleotide in the nucleic acid to be sequenced. In general, a test reaction comprises a polymerase, an exonuclease, and a deoxynucleoside triphosphatase (such as dATP, dCTP, dTTP, or dGTP). A complementary nucleotide is incorporated into the primed growing DNA molecule that is terminated with a nuclease resistant base through the action of a polymerase enzyme. Typical useful polymerase enzymes include DNA polymerases, such as for example, E. coli DNA polymerase I and the commercially available 9 N and Therminator DNA polymerases (available from New England Biolabs, Inc., Beverly, Mass.). Thus, for example, where there is a cytosine on the strand to be sequenced, a guanine will be incorporated, where there is a thymidine, an adenosine will be incorporated, and vice versa. If the nucleoside triphosphate is incorporated into the growing strand in the test reaction, then a pyrophosphate ion (i.e., a pyrophosphate, PPi, or $P_2O_7^{-4}$) is released. In an amplification reaction, an exonuclease is used to remove the incorporated nucleoside monophosphate ($dNMP^{-2}$), allowing another complementary nucleoside triphosphate to be incorporated and a second PPi to be released. Repetition of these addition and excision reactions provides amplification of reaction products. Thus, a positive test reaction (i.e., the detection of chemically amplified products) indicates that the base on the template DNA strand to be sequenced immediately after the priming base (the 3' base) of the primer strand is complementary to the test base (the one of four dNTPs that was used in the synthesis and deconstruction reaction). To sequence the next base on the template, the first identified base on the primer strand is filled or replaced with a nuclease-resistant nucleotide that then becomes the priming base for the test reaction. Nuclease-resistant nucleotides can be ribonucleotides or other modified nucleotides. A variety of polymerases are available that can incorporate ribonucleotides or modified nucleotides into DNA, such as for example, the commercially available Therminator DNA polymerase (available from New England Biolabs, Inc., Beverly, Mass.). See also, for example, DeLucia, A. M., Grindley, N. D. F., Joyce, C. M., *Nucleic Acids Research*, 31:14, 4129-4137 (2003); and Gao, G., Orlova, M., Georgiadis, M. M., Hendrickson, W. A., Goff, S. P., *Proceedings of the National Academy of Sciences*, 94, 407-411 (1997). Exemplary nuclease resistant bases include alpha-phosphorothioate nucleotides, and exemplary nucleases that cannot digest these resistant bases include exonuclease III. Reactions in which no product is detected indicate that the test reaction provided a nucleotide that was not complementary to the next base of the nucleic acid to be sequenced.

Figure 3:
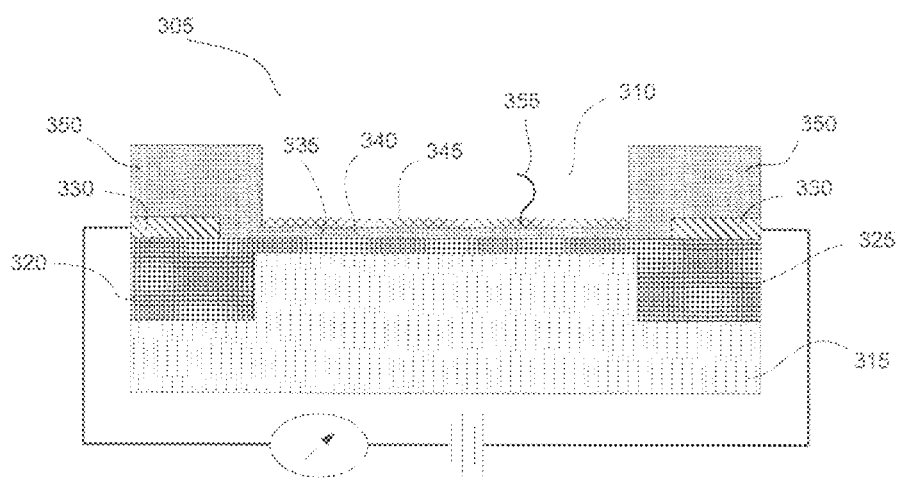
FIG. 3 shows an exemplary electronic detector that is useful as a biosensor.

FIG. 3 diagrams an exemplary sensor unit that is capable of performing as a biosensor for applications such as nucleic acid sequencing and disease identification. In general, FIG. 3 shows a FET (field effect transistor)-based device 305 that is capable of sensing the presence of pyrophosphate ions in a solution to be analyzed (not shown) that is placed in the optional device well 310. The amplified chemical signals created in the well 310 from the nucleic acid synthesis reactions are converted into an electronic signal by the electronic sensor 305. The sensor 305 can be a P-type FET, a N-type FET, a carbon nanotube transistor, or a graphite transistor. See, for example, Janicki, M., Daniel, M., Szermer, M., Napieralski, A., *Microelectronics Journal*, 35, 831-840 (2004) and Rolka, D., Poghossian, A., Schoning, M., *Sensors*, 4, 84-94 (2004). In additional embodiments the sensors are microfabricated metal electrodes made up of a metal such as Au or Pt, in which the electrode metal (not shown) is deposited on top of a channel region of an FET. In this instance the metal electrode becomes the extended gate of the FET device. In one embodiment, the sensor 305 has a nano-sized reaction well 310 and a semiconductor transistor that are separated by an insulating layer. The FET-based device 305 comprises a substrate 315, a source 320, a drain 325, conducting electrodes 330 (comprised of a metal such as, for example, gold, copper, silver, platinum, nickel, iron, tungsten, aluminum, or titanium metal), and a sensing region 335. The sensing region 335 (or "channel") is typically comprised of a doped semiconductor material coated with a thin layer of insulating material 340 (such as, for example, silicon dioxide, silicon nitride, aluminum nitride, and or silicon oxynitride) to which is attached a layer of chelating molecules 345. The channel 335 of the semiconductor transistor, for example, can be comprised of a P- or N-type semiconductor, as is well known in the art, such as for example, silicon or germanium doped with boron, arsenic, phosphorous, or antimony. In general, in a FET, the electric field created by materials located in proximity to the sensing region 335, such as the materials in the optional well 310 and or materials attached directly onto the insulating material 340 (or metal layer (not shown)), such as, in this embodiment of the invention, the chelating molecules 345, change the conductivity of the sensing channel 335. The change in conductivity through the sensing channel 335 is measured and used as a signal that the chelating molecules 345 have bound pyrophosphate. Advantageously, in this embodiment of the present invention, materials to be sensed, such as the chelating molecules 345 are located in close proximity to the sensing region thereby providing an amplified signal to be detected. Optionally, the biosensor comprises a well 310 created by surrounding inert sides 350, comprised, for example, of silicon dioxide, in which reagents can be contained. In alternate embodiments, sensors and arrays of sensors comprise a flat surface instead of a well or depression for the sensing region. Also optionally, a nucleic acid 355 or other molecule to be analyzed is attached above the sensing region 335. In other embodiments, the nucleic acid or other molecule to be analyzed is attached to, for example, a surface located above the sensing region 335 or on a side wall of the well. Advantageously, sensors designed so that they collect molecules to be detected near the sensing region, such as those of the present invention, provide large enhancements in detection sensitivity over sensors that detect molecules that are in a solution. Typically biosensors form part of an array of biosensors housed in a substrate. The substrate is comprised of, for example, silicon, silica, quartz, germanium, or polysilicon and houses electronics capable of addressing the biosensors. Optionally, electronics providing more functionality, such as signal processing and computing ability to drive sample and reagent addition to the biosensors, are also housed in the substrate.

In embodiments of the invention, electronic sensors are arrays of individually-addressable sensors. Arrays are built having a variety of dimensions and numbers of electronic sensor regions. The selection of number layout of sensors is informed by factors such as, for example, the types of analytes to be tested and costs involved in manufacturing the arrays. For example, arrays of sensors are 10×10, 100×100, 1,000×1,000, $10^5 \times 10^5$, and $10^6 \times 10^6$. In general, FET-based electronic sensors are connected to a source line and a drain line. Electronic sensors are monitored individually or as a group. The sensor array allows, for example, many immobilized DNA molecules to be sequenced simultaneously. The immobilized DNA molecules can either be a sample to be sequenced or capture DNA probes of known sequence can be first immobilized and then the sample to be sequenced can be hybridized to the immobilized probes. The capture probes have a sequence designed to hybridize to sections of the sample DNA. Typically, DNA fragments to be immobilized are diluted so that statistically each sensor has one DNA molecule immobilized. Information from electronic sensors showing ambiguous results is disregarded. Sequence information is assembled from the sensors having a single DNA molecule immobilized. Chemical information, such as for example a change in pH or in ionic concentration, from each reaction cavity is sensed independently. Micro- and nanostructures on the array are optionally built to minimize diffusion. For example, wells are optionally built over each sensor, the sensor array is placed upside down, well facing down, with the temperature in the down side lower than the chip side, and a low melting point gel (such as low melting point agarose) is used to make the reaction mixture. For a FET-type electronic sensor, a reaction cavity (or well) optionally forms part of the transistor gate. A reaction cavity is of any shape desired, such as circular, oval, rectangular, or other multi-sided configurations. In additional embodiments, no cavity or well is used. Standard silicon and semiconductor processing methods allow a highly integrated sensor array to be made. For example, a 1 $cm^2$ silicon wafer chip can hold as many as $1 \times 10^8$ sensors that are about 1 $\mu m^2$ and that present a 0.1 $\mu m$ opening to the array surface.

In general, arrays of sensors are formed in a pattern or a regular design or configuration or alternatively are randomly distributed sensors. In some embodiments, a regular pattern of sensors are used the sensors are addressed in an X-Y coordinate plane. The size of the array will depend on the end use of the array. Arrays containing from about two to many millions of different discrete sensors can be made. Very high density, high density, moderate density, low density, or very low density arrays are made. Some ranges for very high-density arrays are from about 100,000,000 to about 1,000,000,000 cavities per array. High-density arrays range from about 1,000,000 to about 100,000,000 cavities. Moderate density arrays range from about 10,000 to about 100,000 cavities. Low-density arrays are generally less than 10,000 cavities. Very low-density arrays are less than 1,000 cavities.

In general, reaction cavities are a depression or well in the surface of the substrate that is capable of containing a liquid or gel.

Figure 4:
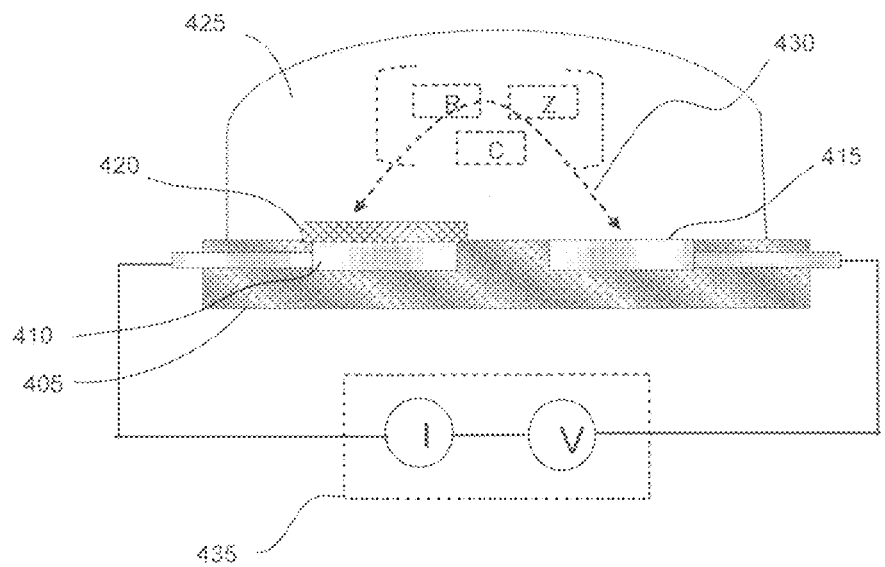
FIG. 4 is an additional exemplary electronic detector that is useful as a biosensor.

In additional embodiments individually-addressable electronic sensors are electrodes. Electrodes are used to measure the impedance (for AC current), the resistance, and or the capacitance of a solution to which they are exposed. In some instances the current at an electrode is measured as a function of applied DC voltage at the electrode-solution interface. Typically, impedance measurements involve measuring the electrical impedance at the electrode-solution interface under AC steady-state conditions and in the presence of a constant DC bias. FIG. 4 provides an exemplary biosensor in which an electrode provides the sensing element. The biosensor of FIG. 4 is optionally one of many biosensors that form an array of biosensors on a substrate. In FIG. 4, a substrate 405 houses a first electrode 410, that functions as the working electrode, and a second electrode 415, that functions as the counter electrode. Additionally, a third electrode (not shown), an electrode that functions as a reference electrode optionally is also used. A layer of chelating molecules 420 is above the working electrode 410. A reaction liquid 425 provides an electrical connection between the working electrode 410 and the counter electrode 415. The molecule(s) to be analyzed (not shown) are attached to the substrate 505, to the working electrode 420, or to another structure (not shown) that forms part of a working sensor device (such as, for example, a microfluidic cavity or channel) so that the molecules to be analyzed are in fluidic contact with the reaction liquid. A hatched arrow 430 shows the movement of current or charge between the electrodes 410 and 415. An electronic circuit 435 measures impedance (Z), capacitance (C), or resistance (R). Typically, the current (I) is detected under varying conditions. The output signal detected from the circuit 435 differs based on the input signal provided to the circuit 435. The input signal differs primarily in frequency and wave shape. Impedance, capacitance, and resistance are calculated based on detected current under a given voltage and frequency. The values calculated depend on the circuit model used. See, for example, Daniels, J. S., Pourmand, N., *Electroanaylsis*, 19, 1239-1257 (2007), Carrara, S., et al., *Sensors & Transducers Journal*, 88, 31-39 (2008), Carrara, S., et al., *Sensors & Transducers Journal*, 76, 969-977 (2007), and Wang, J. Carmon, K. S., Luck, L. A., Suni, I. I., *Electrochemical and Solid-State Letters*, 8, H61-H64 (2005). Optionally the circuit 435 is an integrated circuit. Electronics providing input and output control (not shown) are optionally housed in the substrate, such as in an integrated circuit chip, or are provided through circuitry that is external the substrate.

Electrodes are comprised of conducting materials that are selected to be inert under reaction conditions, such as for example, gold or platinum. In further embodiments the electrodes made from metals, combinations of metals, or other conducting materials. For example, an electrode may be made from, platinum, palladium, nickel, copper, iridium, aluminum, titanium, tungsten, gold, rhodium, as well as alloys of metals, conducting forms of carbon, such as glassy carbon, reticulated vitreous carbon, basal plane graphite, edge plane graphite, graphite, indium tin oxide, conducting polymers, metal doped conducting polymers, conducting ceramics, and conducting clays. The electrode surface is optionally modified, such as for example, through the silanation of the surface as a mechanism to facilitate coupling of molecules to the surface of the sensor.

Many substrate and electrode materials, such as metals, metal oxides, and $SiO_2$, have surface-attached —OH groups that are available for further reaction and molecular coupling. Further, surfaces that present —OH groups for molecular coupling are optionally created on substrate surfaces, through, for example, creating a thin oxide layer on a metal (such as through chemical or plasma etching processes) or through depositing a thin layer of $SiO_2$ onto the surface. If the substrate surface is $SiO_2$, the surface has been coated with $SiO_2$, or the surface is a metal having available —OH groups, molecules are optionally attached to the sensor surface through the use of silane linkers (organo silane compounds). In general, silane linkers are molecules that contain silicon. Useful silane molecules include ones that have at least two different reactive groups bonded to the silane atom of the molecule: Y—R—Si—$(X)_2$. One of the reactive groups, the group represented as X, is capable of bonding to inorganic materials such as glass ($SiO_2$) and metals. These functional groups that are capable of bonding to inorganic materials are groups such as methoxy, ethoxy, chlorine, and silanolic hydroxyl groups. The second functional group, the group represented as Y, is a group such as a vinyl, an epoxy, a methacryl, an amino, a mercapto, or a carboxylic acid group that is capable of forming a chemical bond to an organic material (such as a monomer used to form a polymer). The R group is typically an organic group comprised of from 1 to 10 carbon atoms, such as a straight chain or branched alkane. For example, a silanating agent, such as hydroxypropyltriethoxysilane can be vapor deposited or supplied in a solution to the surface to be silanated. After reaction, the surface presents a —OH group for further molecular coupling. Metal surfaces such as nickel, palladium, platinum, titanium dioxide, aluminum oxide, indium tin oxide, copper, iridium, aluminum, titanium, tungsten, rhodium or other surface having available hydroxy groups or other similar surface groups can also be silanated for further attachment of molecules. In one embodiment of the invention, the surface is a platinum electrode. A very thin layer of oxide can be created on a metal surface, for example, by etching the metal surface with an oxygen plasma or through damascene processes. In additional embodiments, molecules are coupled to sensor surfaces through direct attachment to metal through an electro-grafting or electro deposition process in which an aniline derivative is attached to the sensor surface. See, for example, Pinson, et al., *Chem. Soc. Rev.*, 34, 429-439 (2005); Corgier, et al., *J. Am, Chem. Soc.*, 127, 18328-18332 (2005); and Corgier, et al., *Angew. Chem. Int. Ed.*, 46, 4108-4110 (2007).

In general, electronic sensors employing electrodes are capable of measuring the impedance, the resistance, the capacitance, and or the redox potential of the materials that are located on or near the electrode surface. In embodiments of the present invention, electrodes have chelating molecules attached to the electrode surface. A change in the chemical composition of the chelating molecules (such as through the binding of a pyrophosphate ion) is detected as a change in capacitance at the electrode surface. A device employing electrodes as sensors in some embodiments includes one or more integrating charge amplifiers and is configured to measure the integrated charge and effective capacitance at the analyte-electrode interface. A change in integrated charge or effective capacitance is used to determine whether the attached chelating molecules are chelating pyrophosphate ions. An array of integrating amplifiers and a corresponding electrode array are optionally fabricated on the same substrate. The substrate may also include detection drive circuits, logic for switching, latches, memory, and or input/output devices. The measured capacitance is established by the fixed sensing electrode, the dielectric formed by the attachment chemistry, chelating molecules, and bound analyte (if present), and a virtual parallel plate formed above the sense electrodes by the charge/ion distribution in the solution matrix. The measured capacitance is a function of the electrode area, the dielectric constant, and the distance of the virtual plate (a counter electrode) from the sensing electrode. Analytes binding to the electrode or the attached affinity probe will change the dielectric constant and or the distance between the counter electrode and the sensing electrode, thereby changing the effective capacitance and accumulated charge on the sensing electrode when a voltage is applied. The area and distance to the drive electrode are not material since the conductive matrix carries the voltage to the counter electrode.

Figure 5:
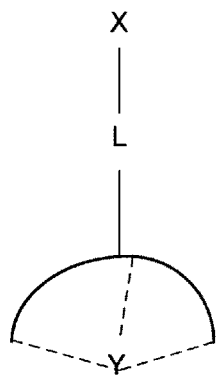
FIG. 5 shows an exemplary diagram of a pyrophosphate chelating molecule that can be attached to a surface.

An exemplary chelating molecule that can be attached to a sensor surface is shown in FIG. 5. In FIG. 5, X represents an surface attachment site for the chelating molecule and can be a group such as, for example, a —$NH_2$ group, an —OH group, a halogen, a thiol, a carboxyl group, an alkyne group, an azido (—$N_3$) an aldehyde, or an —NH—$NH_3$ group. The present invention is not limited by how the chelating molecule is attached to the surface and other attachment chemistries are possible. The "L" in FIG. 5 represents a spacer with functional groups or a linker group and is a group, such as for example, a polyethyle glycol (PEG), polyphosphate $((PO_4)_n)$, a structure such as $(-C-)_n$ which is from 1 to 100 atoms in length and can contain frunctional groups such as amine, hydroxyl, epoxy, aldehyde, carboxyl, and or thiol. Once again, the present invention is not limited in the selection of spacer molecules and other molecules may be used as spacing units. The PPi chelating portion of the molecule (the ligand portion) is represented by the semicircle having an attached Y, in which Y is a cofactor for the chelator such as a metal ion, such as, for example, $Zn^{2+}$, $Cu^{2+}$, and or $Fe^{3+}$. A survey of molecules that are specific PPi chelators can be found in Kim, S. K., et al, *Acc. Chem. Res.*, 42, 23 (2008); and Kruppa & Konig, *Chem. Rev.*, 106, 3520-3560 (2006).

Figure 6:
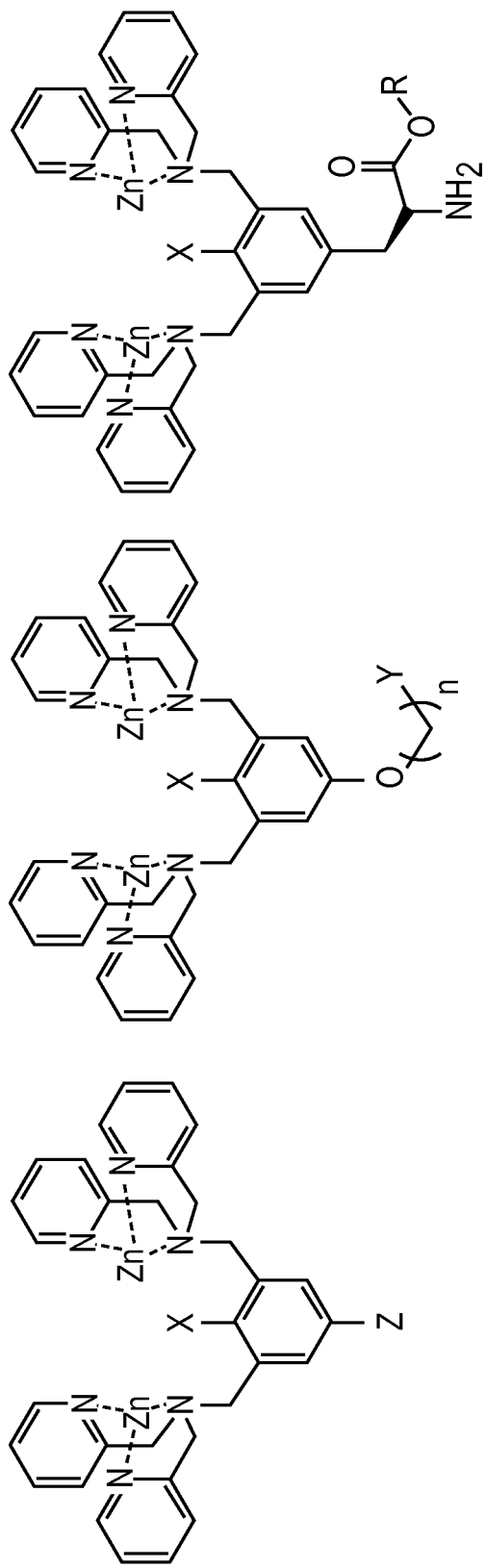
FIG. 6 provides exemplary chelating molecules that can be attached to the surface of a sensing device.

FIG. 6 shows three exemplary chelating molecules that are capable of being attached to a sensor surface. In FIG. 6, X is —H or —OH, R is a —$CH_3$, —$CH_2CH_3$, -t-butyl group, or other functional group comprised of from 1 to 5 carbon atoms wherein one or two carbon atoms is optionally replaced with an oxygen atom, and Y is —$NH_2$, —COOH, —$N_3$, —OH, an aldehyde containing group comprised of between 2 and 10 carbon atoms, a ketene group comprised of between 3 and 10 atoms, a —SH group, an isocyanate group, an isothiocyanate group, or a maleimide group, n is an integer from 1 to 10, and Z is —$NH_2$, —COOH, —$N_3$, —OH, an aldehyde containing group comprised of between 2 and 10 carbon atoms, a ketene group comprised of between 3 and 10 atoms, —SH, an isocyanate group, an isothiocyanate group, or a maleimide group. In additional embodiments, the linker between Y and O is a PEG linker. The zinc ions ("Zn") shown in FIG. 5 bear a +2 charge. Other functional groups providing different synthetic routes for attachment of the chelator to a sensor surface are possible.

Figure 7:
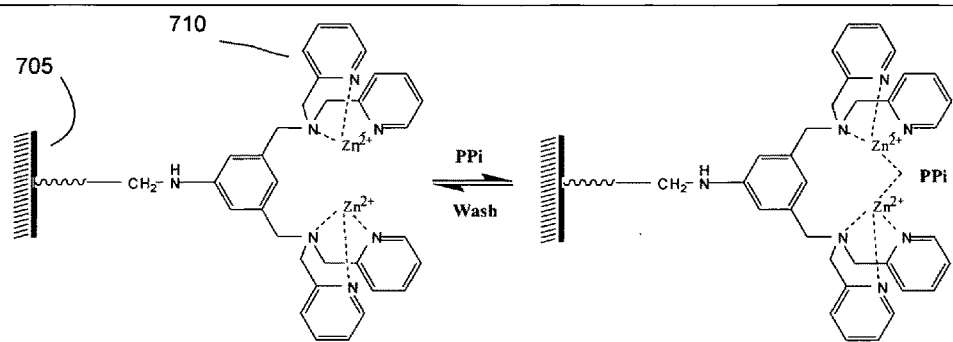
FIG. 7 shows and exemplary chelating reaction that can be detected by an electronic sensor.

FIG. 7 provides an exemplary reaction that can be sensed by an electronic sensor and used in the sequencing of nucleic acids and detection of biomolecules according to embodiments of the invention. In FIG. 7, a sensor surface 705 has an attached chelating molecule 710. Typically an electronic sensor is comprised of many more attached chelating molecules. The number of attached chelating molecules depends in part on the surface area of the sensing region, the number of possible attachment sites for chelating molecules, and the sensitivity desired or necessary to be achieved by the device. In the presence of PPi, the chelating molecule 710 chelates a pyrophosphate providing an event that can be detected by the electronic sensor. As mentioned before, the proximity of the event to be detected to the sensor surface 705 enhances the ability of the sensor to detect the pyrophosphate chelation event. In the presence of PPi ions, the chelating molecule 710 binds PPi providing a detectable event. The PPi is then washed from the surface and removed from the chelating molecule 710 providing a sensor that is once again ready to sense the presence of PPi ions.

Figure 8:
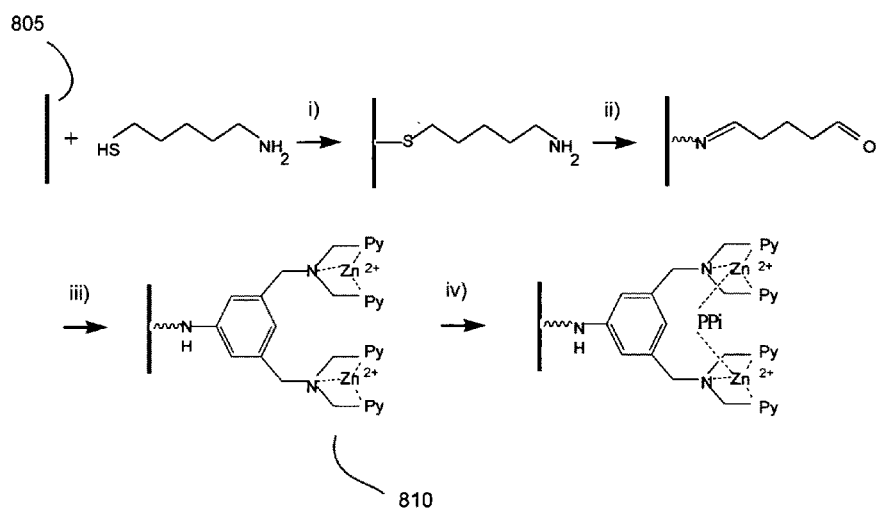
FIG. 8 provides a synthesis scheme demonstrating the attachment of a chelating molecule to a gold electrode sensor surface.

FIG. 8 provides an exemplary attachment scheme for a chelating molecule that is attached to a sensor surface. In the example of FIG. 8, a chelating molecule 810 is attached to a gold electrode surface 805. In FIG. 8, a linking molecule is attached to the gold electrode surface 805 by i) incubating the gold surface with thiolated alkylamine overnight; ii) adding glutaraldehyde and incubating over night; iii) adding a chelator containing an amine group under reducing conditions and incubating for 2-3 hours; and iv) adding $Zn^{2+}$ solution, followed by PPi. An additional example of the attachment of a chelating molecule to a sensor surface is provided in the Examples section and FIG. 11.

Figure 9:
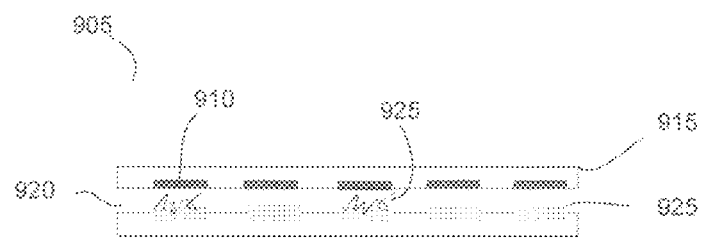
FIG. 9 shows an exemplary electronic sensing device for detecting biomolecules.

FIG. 9 provides a side-view of an exemplary sensor device according to embodiments of the invention. In FIG. 9, the sensor device 905 comprises a plurality of sensor units 910 that make up an array of sensor units 910 housed in substrate 915. Substrate 915 contains electronics (not shown) capable of individually addressing sensor units 910. Optionally, sensor device 905 is part of a microfluidic device (not shown) through which reagents are provided to the sensing region 920. Sensor devices, in general, are provided with a plurality of sensing units 910, and the selection of the number of sensing units 910 depends on factors such as cost, accuracy desired (e.g., for more accurate sensing redundant sensor reactions are employed), and number of different types of reactions to be sensed. Although, it should be noted that sensing devices comprising one sensing region are also possible. Additionally, although a side-view is provided, the pattern of sensor units 905 in substrate 915 is linear, square, or rectangular. Sensor units 910 are, for example, electrodes, FETs, and or extended gate FETs. The sensor units 910 comprise surface-attached PPi chelating molecules (not shown). Sensing region 920 is a chamber to which aqueous reagents are provided from microfluidic channels or reservoirs (not shown). Although in this embodiment the biomolecule to be detected is not located in the same molecular structure layer as the chelators, embodiments are also possible in which the biomolecule to be detected is located in the same molecular structure layer as the chelators. In general, to optimize the sensing configuration, the biomolecules to be detected are located from 0 nm to 100 nm from the sensor surface. In additional embodiments the biomolecules to be detected are located from 0 nm to 10 nm from the sensor surface. Sensor units are also provided having bioanalyte attachment sites 925 which are capable of binding a bioanalyte to be detected or a nucleic acid to be sequenced 930. The bioanalyte attachment sites 925 comprise, for example, an affinity probe such as an antibody or a nucleic acid primer molecule. A nucleic acid primer molecule is terminated with a nuclease resistant nucleotide or a nuclease resistant nucleotide is added to the primer after hybridization of a complementary nucleic acid to be analyzed. Optionally, the sensor device additionally comprises heating and or cooling elements (not shown) that are capable of controlling the temperature of the sensing region 920. The detection of chemical changes within the sensor is performed in real time as concentrations of enzymatic products increase or at the end of the reactions. Advantageously, the biosensor of FIG. 9 can be made as a part of a portable biosensing device.

Figure 10:
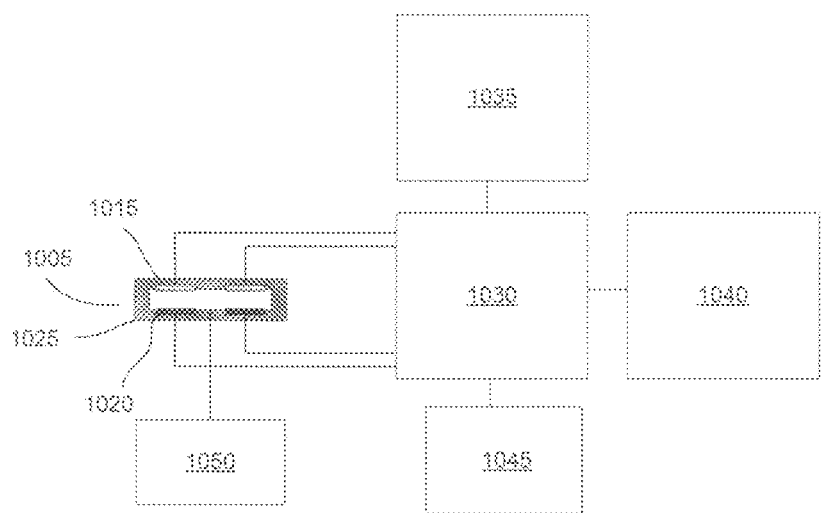
FIG. 10 shows an exemplary electronic sensing device and system for detecting biomolecules

FIG. 10 diagrams an exemplary system apparatus for biosensing that is optionally fabricated as a portable device. In FIG. 10 a sensor device 1005 is electronically coupled to electronic circuitry for signal detection and thermal control 1030. The sensing device 1005 has sensing elements 1015 that are electronic sensors having attached PPi chelators. Recognition and binding sites for molecules of interest (not shown) are provided within the sensor device 1005 in proximity to the electronic sensors 1015. Optionally the sensor device 1005 is a disposable unit that is removed once testing is finished and replaced with a new sensor device capable of testing additional or different molecules. Thermal elements 1020 are located within the sensing device 1005 or within the housing 1025 of sensing device 1005. Exemplary methods of controlling the temperature of the sensor device include using thin metal films of Au, Ag, or Pt as resistive heaters and using a separate metal film (Pt or Au) as a temperature sensor to provide temperature feedback to the control circuitry 1030. In additional embodiments, surrounding temperature control is provided. Surrounding temperature control consists of providing heating or cooling the sensor device 1005 through, for example, a thermal electric coupler (TEC) device (not shown) that is directly coupled to the sensor device 1005. Electronic circuitry 1030 couples the sensing device 1005 to computing elements capable of running control software 1035 and provides for drive power inputs for the sensors, signal detection, and thermal control. Some or all of the electronic circuitry 1030 is optionally located within the sensing device 1005. Control software 1035 provides a user operation interface and controls temperature regulation functions, fluidic reagent delivery operations, and data collection, output, analysis, display, and storage operations. A storage device 1040 stores for example software code, run routines, and collected data. A power source 1045 provides power to the system including an AC/DC converter and optionally a battery. Fluidic and reagent delivery systems 1050 provide reagents to the sensing device 1005. Fluidic and reagent delivery is accomplished with micofluidic or nanofluidic devices. Fluidic delivery systems optionally include reservoirs for holding reagents. Optionally, the system also includes a de-gassing system to remove gasses from fluids and prevent bubble formation, a mixer for reagent mixing, and a micro cooler for reagents to maintain reagent integrity.

Electronic pyrophosphate biosensors according to embodiments of the invention are capable of performing a variety of biologically important detections. For example, electronic pyrophosphate biosensors are capable of detecting mutations in DNA and identifying pathogens through DNA sequencing reactions. Additionally, electronic biosensors are used to diagnose diseases through assaying metabolic enzyme activities. Pyrophosphate is a byproduct of many enzymatic reactions that are part of metabolic and signal transduction pathways. Electronic biosensors according to FIGS. 3, 7, 8, 9 and 10 are optionally designed to provide recognition and binding sites for a target analyte. Alternatively, the binding site for the analyte is located in proximity to the sensor, in close enough proximity to the electronic sensor that PPi generated is detected by the electronic sensor. In general, the biomolecule to be senses is located from 0 nm to 100 nm from the sensor surface. Typically, less than 10 target analyte molecules are bound in proximity to a sensor and the reaction product PPi molecules are sensed by the sensor. In some applications one molecule is bound in proximity to a sensor and is sensed by the sensor (through the detection of PPi produced in a reaction). In further alternate embodiments the analyte molecule is not located in proximity to the sensor, and a reactions solution from the analyte region is flowed over the surface of the electronic sensor to enable sensing of PPi in a reactant solution. The biosensor device is created having the recognition and binding site of interest and a test is performed on a sample solution by exposing the sample solution to the analyte binding region of the biosensor device to allow binding of any specifically recognized biomolecules of interest. The biosensor device is optionally a micro- or nanofluidic device that provides filtering and sample purification functions. Thus, an enzyme to be tested for functionality is bound in the electronic biosensor and a reaction solution is provided in which a reaction product is PPi. For example, a biosensor device probes the functionality of adenylating enzymes that convert fatty acids to acyl adenylate and produce PPi by binding the adenylating enzyme of interest in the biosensor device and providing fatty acid substrates as well as ATP in a reaction solution. In additional examples, living microbes are specifically bound to biosensors and released ATP is detected through the enzymatic conversion of ATP by aparase to PPi. Microbes are optionally bound in the sensing device through an antibody that specifically recognizes a surface antigen on the microbe. In further examples, antibody sandwich assays are performed. In the antibody sandwich assay, an electronic sensor is provided having an antibody specific for the molecule to be detected, the sensor is exposed to the molecule to be detected, and a second antibody specific for a different epitope of the molecule to be detected is bound to the molecule to be detected. The second antibody has an attached DNA molecule. Nucleic acid amplification is performed on the attached DNA molecule, generating PPi ions that are detected by the biosensor.

In general, a molecular attachment site is a surface-attached chemical functional group or molecule that allows the addition of a monomer, linker, nucleic acid, protein, or other molecule to the surface of the substrate. The molecular attachment site comprises, in some embodiments, a reactive functional group that allows molecular addition or coupling. The molecular attachment site may be protected or unprotected. Substrate and electrode surfaces are functionalized, for example, with one of or a combination of amine, aldehyde, epxoy, and or thiol groups, and molecules to be attached are functionalized with amine (for surface bearing carboxy, epoxy, and or aldehyde functional groups) and carboxyl (for surface bearing amine groups), thiol (for surface of gold) to create molecular attachment sites. Various conjugation chemistries are available to join the functional groups (for example, EDC for amine-carboxyl). The concentration of molecules on the substrate surface is controlled, for example, in several ways: by limiting the density of surface functional groups or by limiting the quantity of molecules to be attached. In some embodiments, a molecular attachment site is a biotin molecule and the molecule to be attached is coupled to an avidin (or streptavidin) molecule.

In general, nucleic acid attachment sites are sites on a substrate surface that present functional groups, nucleic acids, affinity molecules, or other molecules that are capable of undergoing a reaction that attaches a nucleic acid to a substrate surface. DNA molecules are immobilized on a substrate or sensor surface by standard methods, such as, for example, through biotin-avidin or antibody-antigen binding. Biotin, avidin, antibodies, or antigens are attached, for example, to an insulating layer comprised of silicon oxide through derivatization of the silica surface with, for example, (3-aminopropyl)triethoxysilane to yield a surface that presents an amine group for molecule attachment. Molecules are attached by using water-soluble carbodiimide coupling reagents, such as EDC (1-ethyl-3-(3-dimethyl aminopropyl) carbodiimide), which couples carboxylic acid functional groups with amine groups. DNA molecules bearing a corresponding coupling group are then attached to the surface through, for example, a biotin-avidin or antibody-antigen interaction. Additionally, acrydite-modified DNA fragments are attached, for example, to a surface modified with thiol groups, and amine-modified DNA fragments are attached, for example, to epoxy or aldehyde modified surfaces. The nucleic acid attachment site is also a nucleic acid that is capable of hybridizing a nucleic acid to be attached to a surface.

A recognition (binding) site is a molecular attachment site that is a surface-attached molecule that is capable of specifically recognizing and binding a desired molecule. In the case of a nucleic acid, the recognition or binding site is, for example, a complementary nucleic acid that is capable of specifically hybridizing the nucleic acid of interest. In the case of a protein or peptide, the recognition or binding site is a molecule that specifically binds with the protein or peptide of interest, such as for example, a ligand for the protein (or peptide) or an antibody.

In alternate embodiments, electronic sensors are fabricated without attached chelating molecules and PPi that is generated by reactions that are proximate to the sensor surface is precipitated out onto the sensor surface. The PPi molecule is precipitated out onto the sensor surface using, for example, molybdenum blue.

In additional embodiments, the sensor can comprise a carbon nanotube or graphene transistor. Carbon nanotube FET devices have been described. See, for example, Star, A., Gabriel, J. P., Bradley, K., Gruner, G., *Nano Letters,* 3:4, 459-463 (2003) and Fritz, J, Cooper, E. B., Gaudet, S., Sorger, P. K., Manalis, S. R., *Proceedings of the National Academy of Sciences,* 99:22, 4984-4989 (2002). In general, carbon nanotubes, such as for example, single-walled carbon nanotubes (SWNTs), that are useful in a FET device, can be made through the chemical vapor deposition of methane onto catalytic iron nanoparticles. Metal evaporation through a mask can be used to create the electrical contacts that form a source and a drain. DNA can be attached to the carbon nanotube transistor, for example, by coating the carbon nanotube with Tween-20 or polyethylene oxide, which readily adsorb to the surface of the nanotube, activating the Tween-20 or polyethylene oxide-containing polymer with a water-soluble carbodiimide coupling reagent, such as for example, 1,1-carbonyldiimidazole, for conjugation with coupling agents such as biotin, avidin, antigens, or antibodies. DNA molecules having a corresponding coupling agent can then be attached through the surface through, for example, a biotin-avidin or antibody-antigen interaction. Carbon nanotube or graphene transistors having attached PPi chelating molecules are fabricated by 1) functionalizing the carbon nanotube or grapheme surface with strong acid (sulfuric acid/nitric acid) to attach carboxyl groups (—COOH) on its surface; 2) introducing amine groups via EDC-mediated bisamine coupling; 3) introducing aldehyde groups under reducing condition with glutaraldehyde; and then 4) adding amine-functionalized PPi chelator under reducing conditions.

There are numerous suitable methods for patterning an array of nanoscale features on a surface of a substrate. Examples of such suitable methods include lithography methods such as, for example, interferometric lithography (IL), immersion interferometric lithography, electron beam lithography, scanning probe lithography, nanoimprint, extreme ultraviolet lithography, and X-ray lithography, and stamping, etching, microetching, and molding techniques. The technique used will depend in part on the composition and shape of the substrate. Generally, lithography is a highly specialized printing process used to create detailed patterns on a substrate, such as a silicon wafer. An image containing a desired pattern is projected onto the wafer, which is coated by a thin layer of photosensitive material called resist. The bright parts of the image pattern cause chemical reactions which, in turn, render the resist material soluble, and, thus, dissolve away in a developer liquid, whereas the dark portions of the image remain insoluble. After development, the resist forms a stenciled pattern across the wafer surface, which accurately matches the desired pattern. Finally, the pattern is permanently transferred into the wafer surface, for example by a chemical etchant, which etches those parts of the surface unprotected by the resist.

A solid support, support, or substrate is an object having a rigid or semi-rigid surface or surfaces. In some aspects at least one surface of a solid support is planar or substantially planar. The sensing regions of an array of electronic sensors optionally form regions that are for example, wells, depressions, raised regions, pins, or etched trenches. In embodiments of the invention the substrate comprises a silicon wafer or a portion of a silicon wafer. A silicon wafer may also be referred to as a chip or a semiconductor substrate. A wafer or chip may be fashioned in various shapes and sizes. The chip can be overlaid or embedded with circuitry for driving electronic sensors, sensing voltages, microprocessors, memory functions, and input/output capabilities. In embodiments of the invention, the chip comprises at least electronic sensors and embedded circuitry for individually addressing and driving the electrodes and sensing voltages, currents, and or resistances and or circuitry capable of connecting the electrodes to external mechanisms for individually addressing the electrodes, sensing voltages, currents, and or resistances, and driving the electrodes. A substrate may also be comprised of silicon, glass, nylon, plastic or other polymeric material, silicon nitride, metals, metal oxides, metal nitrides, or combinations thereof.

In various embodiments of the invention, arrays may be incorporated into a larger apparatus and/or system. In certain embodiments, the substrate may be incorporated into a micro-electro-mechanical system (MEMS). MEMS are integrated systems comprising mechanical elements, sensors, actuators, and electronics. All of those components may be manufactured by known microfabrication techniques on a common chip, comprising a silicon-based or equivalent substrate (See for example, Voldman et al., *Ann. Rev. Biomed. Eng.*, 1:401-425 (1999).) The sensor components of MEMS may be used to measure mechanical, thermal, biological, chemical, optical and/or magnetic phenomena. The electronics may process the information from the sensors and control actuator components such as pumps, valves, heaters, coolers, and filters, thereby controlling the function of the MEMS.

The electronic components of sensors and MEMS devices are fabricated using, for example, integrated circuit (IC) processes (for example, CMOS, Bipolar, or BICMOS processes) used for chip manufacture. The components are patterned using photolithographic and etching methods known for computer chip manufacture. The micromechanical components are fabricated using compatible micromachining processes that selectively etch away parts of the silicon wafer or add new structural layers to form the mechanical and/or electromechanical components.

Basic techniques in chip manufacture include depositing thin films of material on a substrate, applying a patterned mask on top of the films by photolithographic imaging or other known lithographic methods, and selectively etching the films. A thin film may have a thickness in the range of a few nanometers to 100 micrometers. Deposition techniques of use may include chemical procedures such as chemical vapor deposition (CVD), electrodeposition, epitaxy and thermal oxidation and physical procedures like physical vapor deposition (PVD) and casting.

In some embodiments of the invention, substrates are connected to various fluid filled compartments, such as reservoirs, microfluidic channels, nanochannels, and or microchannels. These and other components of an electronic sensor device apparatus are manufactured to be a single unit, for example in the form of a chip, such as semiconductor chips and or microcapillary or microfluidic chips. Alternatively, the substrates are removed from a silicon wafer and attached to other components of an apparatus. Any materials known for use in such chips may be used in the disclosed apparatus, including silicon, silicon dioxide, silicon nitride, polydimethyl siloxane (PDMS), polymethylmethacrylate (PMMA), plastic, glass, and quartz.

The sensing regions of an array of electronic sensors may have any convenient shape, for example, circular, square, rectangular, elliptical, or wedge-shaped. In some embodiments, the electronic sensing region is smaller than about 1 mm$^2$ or less than 0.5 mm$^2$. In further embodiments the sensing regions have an area less than about 10,000 µm$^2$ or less than 2.5 µm$^2$. Advantageously, the present invention is not limited to a particular size or configuration for the array.

An array of sensing electrodes is optionally equipped with circuitry for individually addressing the electrodes, driving the electrodes at selected voltages (or set current values corresponding to the desired voltage), memory for storing voltage current information to be supplied to the electrodes, memory and microprocessors for measuring electrode characteristics, differential amplifiers, field effect transistors (direct and floating gate). Alternatively, one or more of these functions can be performed by an attached computer system.

Electrode surfaces are optionally functionalized, for example, with one of or combination of amine, aldehye, epxoy, thiol, groups, and molecules to be attached are functionalized with amine (for surface bearing carboxy, epoxy, and or aldehyde functional groups) and carboxyl (for surface bearing amine groups), thiol (for surface of gold) to facilitate molecular attachment. Various conjugation chemistries are available to join the functional groups (for example, EDC for amine-carboxyl). The concentration of molecules on the substrate surface is controlled, for example, in several ways: by limiting the density of surface functional groups or by limiting the quantity of molecules to be attached. DNA is immobilized on a surface, for example, by using acrydite-modified DNA fragments that are attached to a surface modified with thiol groups. Amine-modified DNA fragments can be attached to epoxy or aldehyde modified surfaces.

In general, the types of nucleic acids that can be sequenced include polymers of deoxyribonucleotides (DNA) or ribonucleotides (RNA) and analogs thereof that are linked together by a phosphodiester bond. A polynucleotide can be a segment of a genome, a gene or a portion thereof, a cDNA, or a synthetic polydeoxyribonucleic acid sequence. A polynucleotide, including an oligonucleotide (for example, a probe or a primer) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine, or uracil linked to ribose. However, a polynucleotide or oligonucleotide also can contain nucleotide analogs, including non-naturally occurring synthetic nucleotides or modified naturally occurring nucleotides.

The covalent bond linking the nucleotides of a polynucleotide generally is a phosphodiester bond. However, the covalent bond also can be any of a number of other types of bonds, including a thiodiester bond, a phosphorothioate bond, a peptide-like amide bond or any other bond known to those in the art as useful for linking nucleotides to produce synthetic polynucleotides. The incorporation of non-naturally occurring nucleotide analogs or bonds linking the nucleotides or analogs can be particularly useful where the polynucleotide is to be exposed to an environment that can contain nucleolytic activity, since the modified polynucleotides can be less susceptible to degradation.

Virtually any naturally occurring nucleic acid may be sequenced including, for example, chromosomal, mitochondrial or chloroplast DNA or ribosomal, transfer, heterogeneous nuclear or messenger RNA. RNA can be converted into more stable cDNA through the use of a reverse transcription enzyme (reverse transcriptase). Additionally, non-naturally occuring nucleic acids that are susceptible to enzymatic synthesis and degredation may be used in embodiments of the present invention.

Methods for preparing and isolating various forms of nucleic acids are known. See for example, Berger and Kimmel, eds., *Guide to Molecular Cloning Techniques*, Methods in Enzymology, Academic Press, New York, N.Y. (1987); Sambrook, Fritsch and Maniatis, eds., *Molecular Cloning: A Laboratory Manual, 2nd Ed.*, Cold Spring Harbor Press, Cold Spring Harbor, N.Y. (1989); and Ausbel, F. M., et al., eds., *Current Protocols in Molecular Biology*, Wiley and Sons, Inc. (2007). Samples comprising RNA can be converted to DNA for sequencing using a reverse transcriptase enzyme to synthesize a complementary strand of DNA from the RNA molecule. Commercial kits for preparing nucleic acids are available, such as, for example, the SuperScript™ Double-Stranded cDNA Synthesis Kit from Invitrogen.

Typical useful polymerase enzymes include DNA polymerases with or without 3' to 5' exonuclease activities, such as for example, E. coli DNA polymerase I, Klenow fragment of E. Coli DNA polymerase I, phusion DNA polymerase, 9 N and Therminator DNA polymerase, reverse transcriptase, Taq DNA polymerase, Vent DNA polymerase (all available from New England Biolabs, Inc., Beverly, Mass.), T4 and T7 DNA polymerases, and Sequenase (all available from USB, Cleveland, Ohio). Nuclease-resistant nucleotides can be ribonucleotides or other modified nucleotides. A variety of polymerases are available that can incorporate ribonucleotides or modified nucleotides into DNA, such as for example, the commercially available Therminator DNA polymerase (available from New England Biolabs, Inc., Beverly, Mass.) or genetically engineered DNA polymerase. See also, for example, DeLucia, A. M., Grindley, N. D. F., Joyce, C. M., *Nucleic Acids Research*, 31:14, 4129-4137 (2003); and Gao, G., Orlova, M., Georgiadis, M. M., Hendrickson, W. A., Goff, S. P., *Proceedings of the National Academy of Sciences*, 94, 407-411 (1997). Exemplary nuclease resistant nucleotides that can be incorporated into growing DNA strands but that are resistant to digestion by exonucleases (such as the 3' to 5' exonuclease active DNA polymerases or exonuclease I and III) include alpha-phosphorothioate nucleotides (available from Trilink Biotechnologies, Inc., San Diego, Calif.). Additionally, ribonucleotides can be incorporated into a growing DNA strand by Therminator DNA polymerase or other genetically engineered or mutated polymerases. Phi-29 DNA polymerase (available from New England Biolabs) provides strand displacement activity and terminal deoxynucleotide transferase provides template independent 3' terminal base addition.

EXAMPLES

Synthesis and Attachment of Pyrophosphate Chelators to a Substrate Surface

Figure 11:
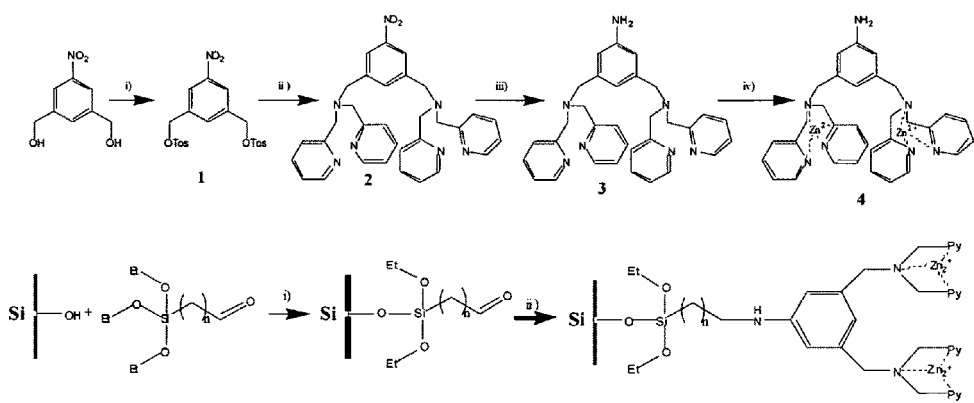
FIG. 11 shows an exemplary synthesis scheme for a surface-attached pyrophosphate chelating molecule.

The pyrophosphate chelator was designed with three main components: a binding site, a linker, and a handle. The binding site was designed to bind PPi selectively, the linker between the binding site and chelator was designed to provide steric flexibility to the overall molecule if needed, and the handle was designed to ensure that the chelator can be attached to a surface. The selected PPi chelator has demonstrated high binding capability to PPi. Referring to FIG. 11, the starting material for the synthesis of the surface-attachable pyrophosphate chelator was 5-nitro-1,3-bishydroxymethylbenzene. The hydroxyl groups of the 5-nitro-1,3-bishydroxymethylbenzene were tosylated with TosCl (tosylchloride) to accelerate the substitution reaction in the next synthesis reaction. The tosylate groups were replaced by dipyridinylamines using di-(2-picolyl)amine. The nitro group was reduced efficiently to an amine group by catalytic hydrogenation using Pd/C and $H_2$. The zinc nitrate ($Zn(NO_3)_2$) was added afterwards to yield a functional pyrophosphate chelator capable of being attached to a substrate surface.

The synthesized pyrophosphate chelator was immobilized on a silicon substrate surface that had been silanated. An aldehyde group was used to functionalize the silicon surface through derivatization of the silicon surface with 4-(triethoxysilyl)butyraldehyde in ethanol. Reductive amination with sodium triacetoxyborohydride ($NaBHAc_3$) at pH 8 was used to covalently attach the pyrophosphate chelator to the derivatized substrate surface. Immobilization of the pyrophosphate chelator was confirmed: the substrate surface was characterized by ellipsometry, atomic force microscope (AFM) and TOF-SIMS (time-of-flight secondary ion mass spectroscopy). Monolayer thicknesses and sample topography were consistent with step-by-step surface modification of silicon substrate surface. Ellipsometry and AFM data indicated a thickness of about 35 Å for the pyrophosphate chelator and its linker, consistent with the expected value. TOF-SIMS measurements of modified substrate surfaces yielded the expected mass of the immobilized pyrophosphate chelator while the pyrophosphate chelator was not detected on several types of control samples.

Binding Kinetics:

The newly synthesized immobilizable pyrophosphate chelator was subjected to selective binding studies using a coumarin-based fluorescent dye, (6,7-dihydoxy-2-oxo-2H-chromen-4-yl)methanesulfonate, and a colorimetric dye, pyrocatechol violet (PV). In case of fluorescent dye, binding to the chelator caused quenching of its fluorescence. As more chelator was added, fluorescence intensity decreased showing dose response as expected that reached a plateau near 10 μM. The dose response curve was used to estimate the binding constant for this fluorescent dye at $1.7 \times 10^6$ $M^{-1}$. This binding constant was similar to what was reported for a similar pyrophosphate chelator. When the colorimetric dye was used, the binding to pyrophosphate chelator caused a detectable color change from blue (free dye, $\lambda_{max}$ 444 nm) to yellow (complex, $\lambda_{max}$ 624 nm). The peak absorption change from blue (free dye, $\lambda_{max}$ 444 nm) to yellow ($\lambda_{max}$ 624 nm) indicated formation of chelator-dye complex. This color change was visible to naked eye.

To study selectivity of the immobilizable pyrophosphate chelator, the binding of PPi to the chelator was compared to the binding of phosphate (Pi) and dATP. Both fluorescence and absorption data indicated that the chelator showed selectivity for PPi over Pi and dATP. A competitive displacement assay of the immobilizable chelator with PPi, dATP, and Pi was performed. 1:1 mixtures of chelator and fluorescent dye were treated with various concentrations of binders. Fluorescence was monitored at 480 nm with excitation at 347 nm. Other dNTPs were also studied in competitive displacement assays. The immobilizable chelator was found to bind PPi preferentially over other dNTPs, similar to the results for dATP.

Figure 12:
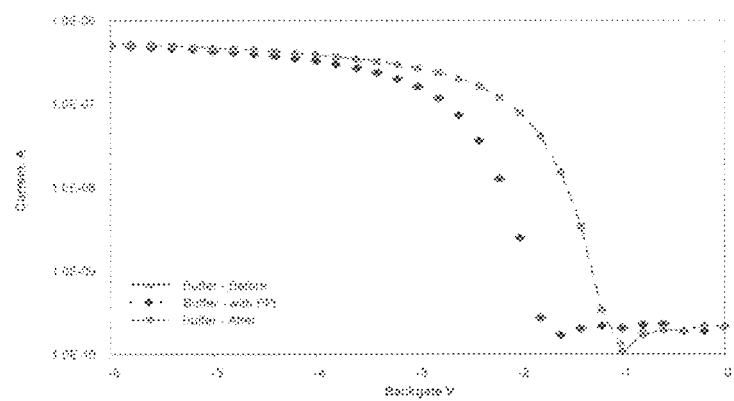
FIG. 12 graphs the results of the electronic detection of pyrophosphate ions by a p-type field-effect transistor device having surface-attached pyrophosphate chelating molecules.

To demonstrate the signal immobilization function of this newly synthesized immobilizable chelator, pyrophosphate sensing was performed using a silicon-on-insulator field effect transistor (SOI-FET) device. FIG. 12 graphs the measured signals. Measurements were performed before addition of PPi to the sensor (curve labeled "Buffer—Before" in FIG. 12). The FET device having surface-attached chelators in the sensing region was then exposed to 25 μM of PPi in tris buffer (pH 8). After exposure to a PPi-containing solution the drain current versus gate potential plot shifted towards more negative potentials (FIG. 12, curve labeled "Buffer—with PPi"), consistent with a field-effect caused by the binding of PPi to chelator on the sensor surface. This shift was observed repeatedly in different devices and was reversible if the substrate was exposed to an acidic rinse. The sensor surface was washed with an acidic rinse to remove chelated PPi. Measurements taken after washing the surface are shown in FIG. 12, curve labeled "Buffer—After." FET devices modified with the same silane, but terminated with PEG blocking molecules instead of PPi-sensitive chelator, did not respond to the same PPi-containing buffer solution. In addition, unmodified FET devices did not respond to the same PPi solution. PPi accumulation on the sensor surface caused changes in surface charge distribution and, thus, enabled selective electrical detection of PPi. The sensor surface was washed with an acidic rinse to remove chelated PPi. Measurements taken after washing the surface are shown in FIG. 12, curve labeled "Buffer—After."

In further reactions, the FET device having surface-attached PPi chelators was tested for sensing PPi generated from an enzymatic reaction. PPi was accumulated in a nucleic acid synthesis idling reaction in which the primer was nuclease resistant when T4 DNA polymerase and a nucleoside triphosphate were used.

The invention claimed is:

1. A device comprising:
   a substrate comprising a plurality of individually-addressable electronic sensors wherein each electronic sensor has a surface and the sensor surface comprises attached molecules capable of selectively binding pyrophosphate ions,
   attachment sites for nucleic acid molecules to be sequenced wherein one attachment site is located in close proximity to one sensor, wherein in close proximity is between 0 nm to 100 nm of the sensor surface,
   an electronics system operably coupling a computer to the plurality of electronic sensors, and
   the computer capable of receiving, storing, and processing data from the electronics system and capable of assembling the sequence of a nucleic acid molecule to be sequenced wherein assembling the sequence of a nucleic acid molecule includes using data from an individually-addressable electronic sensor indicative of whether or not pyrophosphate ion is bound to the molecules capable of selectively binding pyrophosphate ions on the sensor surface.

2. The device of claim 1 also comprising a fluid delivery system, wherein the fluid delivery system is comprised of a plurality of reservoirs capable of containing a plurality of solutions and a plurality of outlets from plurality of reservoirs capable of delivering fluids to the surface of the substrate.

3. The device of claim 1 wherein the electronics system is capable of causing a solution from a reservoir to be supplied to the surface of the substrate and wherein the computer is capable of directing the electronics system to supply a solution from a reservoir to the surface of the substrate.

4. The device of claim 1 wherein the substrate is comprised of 2 to 10,000 sensors.

5. The device of claim 1 wherein the substrate is comprised of 10,000 to 1,000,000,000 electronic sensors.

6. The device of claim 1 wherein the electronic sensors are field effect transistors, extended gate field effect transistors, electrodes, or combinations thereof.

7. The device of claim 1 wherein the attachment sites for nucleic acid molecules to be sequenced are located on sensor surfaces.

8. The device of claim 1 wherein in close proximity is between 0 nm to 10 nm of the sensor surface.

9. The device of claim 1 wherein the attachment sites for nucleic acid molecules to be sequenced comprise surface-attached DNA molecules.

* * * * *